United States Patent [19]

Carson

[11] Patent Number: 4,585,784
[45] Date of Patent: Apr. 29, 1986

[54] PYRROLE-2-ACETYLAMINO ACID DERIVATIVE COMPOUNDS

[75] Inventor: John R. Carson, Norristown, Pa.

[73] Assignee: McNeilab, Inc., Fort Washington, Pa.

[21] Appl. No.: 461,055

[22] Filed: Jan. 26, 1983

[51] Int. Cl.$^4$ .................. A61K 31/40; C07D 207/333
[52] U.S. Cl. ..................................... 514/423; 548/539
[58] Field of Search .................. 548/539; 424/274; 514/423

[56] References Cited

U.S. PATENT DOCUMENTS

| | | | |
|---|---|---|---|
| 3,336,194 | 8/1967 | Shen | 424/248.54 |
| 3,752,826 | 8/1973 | Carson | 548/539 X |
| 3,962,471 | 6/1976 | Biere et al. | 424/274 |
| 4,379,793 | 4/1983 | Badia et al. | 548/539 X |
| 4,396,626 | 8/1983 | Ward et al. | 548/539 X |
| 4,434,175 | 2/1984 | Doherty et al. | 548/518 X |

FOREIGN PATENT DOCUMENTS 2115417 9/1983 United Kingdom .

OTHER PUBLICATIONS

Massaroli, UK patent application, 12-1-82, G.B. 2,098,989 A, 3 pages.
Burger, Medicinal Chemistry, 3rd ed., Part I, (1970), pp. 50–59, Wiley-Interscience, N.Y.
Abstract of JA-7244221-R (Sumitomo Chem. Co. Ltd.), 8-11-72.

Primary Examiner—Joseph Paul Brust
Attorney, Agent, or Firm—David J. Levy

[57] ABSTRACT

Novel pyrrole-2-acetylamino compounds of the formula:

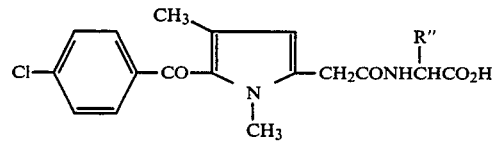

and salts thereof, wherein R'' is H, alkyl, $(CH_2)_nCO_2H$, $CH_2CH_2SCH_3$, $(CH_2)_4NH_2$ or $(CH_2)_2CONH_2$; and n is 1 or 2, which have the same analgesic and antiinflammatory utility as zomepirac, but with reduced liability toward gastrointestinal irritation, and esters of the compounds of the above formula which are useful as intermediates to make said compounds.

7 Claims, No Drawings

PYRROLE-2-ACETYLAMINO ACID DERIVATIVE COMPOUNDS

The present invention comprises novel acylamino acids and their salts wherein the acyl group is [5-(4-chlorobenzoyl)-1,4-dimethyl)-1H-pyrrol-2-yl]-acetyl having the general formula 4 below, and also amide esters thereof having the general formula 3 below which are used as intermediates to make the acids of general formula 4.

Zomepirac (general formula 1 below) is the generic name for the compound [5-(4-chlorobenzoyl)-1,4-dimethyl-1H-pyrrol-2-yl]acetic acid which has analgesic and antiinflammatory activity and which is commercially available as zomepirac sodium dihydrate.

Although zomepirac is used clinically as an analgesic, its mode of action appears to involve inhibition of prostaglandin biosynthesis. Zomepirac shares with other drugs which inhibit prostaglandin biosynthesis the side effect of gastrointestinal irritation. It has now been unexpectedly found that the liability of zomepirac toward gastrointestinal irritation can be reduced if zomepirac is administered in the form of its amide with an amino acid.

The particular amino acid derivatives of zomepirac are the following: glycine, alanine, methionine, glutamic acid, aspartic acid, lysine, and glutamine, and the resultant compounds of the present invention have general formula 4 below, and may be in either optically active or racemic form. They may be administered in the form of their free acids or in the form of their pharmaceutically-acceptable salts, for example, as salts of alkali metals, preferably sodium or potassium, or alkaline earth metals, preferably calcium, or salts of organic amines, preferably 2-amino-2-(hydroxymethyl)-1,3-propanediol (tromethamine). They may be prepared by the following reaction scheme (A):

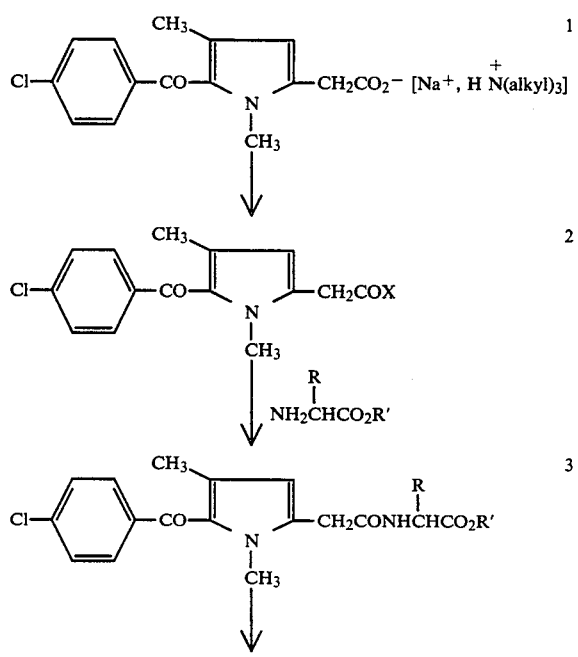

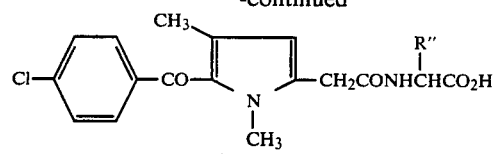

In the above formulae:
X=halide [particularly Cl or Br], —OCH$_2$CN, or —OCOO alkyl
R=H, alkyl, (CH$_2$)$_n$CO$_2$R', CH$_2$CH$_2$SCH$_3$, (CH$_2$)$_4$NHCbZ, or (CH$_2$)$_2$CONH$_2$
n=1 or 2
R'=alkyl or benzyl
R''=H, alkyl, (CH$_2$)$_n$CO$_2$H, CH$_2$CH$_2$SCH$_3$, (CH$_2$)$_4$NH$_2$, or (CH$_2$)$_2$CONH$_2$ When the term "alkyl" is used, it is intended to include C$_1$-C$_6$ alkyls, which can be straight or branched chain, primary, secondary or tertiary, such as methyl, isopropyl, isobutyl, sec-butyl, hexyl and the like alkyls.

Compounds of type 4 may be prepared by the illustrated three-step procedures (1→4). Zomepirac (1) is first converted to an activated derivative (2). Three different types of activated derivatives may be used, namely, the acid halide (2, X=halide), the activated ester (2, X=OCH$_2$CN), or
the mixed carbonic anhydride

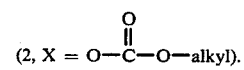

Preparation of acid halides has been previously described [J. R. Carson, U.S. Pat. No. 3,752,826 (1973)]. The activated ester (2, X=OCH$_2$CN) may be prepared by reaction of a zomepirac salt with chloroacetonitrile in a dipolar aprotic solvent (such as, for example, DMSO, DMF, acetonitrile or acetone) at 20° to 80° C. The mixed anhydrides

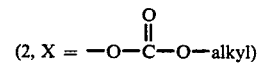

may be prepared by reaction of a zomepirac salt (for example, triethylammonium or N-methylmorpholinium) with an alkyl chloroformate (for example, ethyl chloroformate or isobutyl chloroformate) in an inert aprotic solvent such as THF or methylene chloride) at −50° to −70° C.

In the second step, amino acid esters

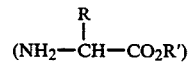

are acylated by the action of an activated zomepirac derivative (2) to give amide esters (3). The amino acid esters may be liberated from their corresponding salts by treatment with an organic tertiary amine such as triethylamine or an inorganic weak base such as an alkali metal bicarbonate or carbonate. Acylations of the amino acid esters using zomepirac acyl halides are carried out in the presence of a hydrogen halide acceptor such as a tertiary amine (e.g., triethylamine) in an inert aprotic solvent at 0° to 80° C. The acylation procedures using the activated esters (2, X=OCH$_2$CN) are carried out in an inert aprotic solvent (for example, THF or dioxane) at elevated temperature (50° to 100° C.), preferably in the presence of a weak organic acid catalyst. The amino acid esters are used in excess. The acylation reaction utilizing the mixed anhydride reagents

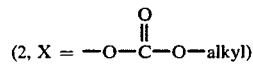

are carried out in inert aprotic solvents, preferably in the same solution in which the reagent is prepared. The temperature range for carrying out acylations using mixed anhydrides is 0° to −75° C. When the amino acid ester being used is a glutamic acid ester, the mixed anhydride route is preferred, and the activated ester route is not used.

The conversion of amide esters 3 to amide acids 4 may be carried out by conventional saponification using about one equivalent of an alkali metal hydroxide in aqueous or mixed aqueous organic solution (e.g., ethanol-water) over a temperature of 25° to 100° C. When R' is benzyl, the generation of 4 may be carried out by treatment with boron tribromide in an inert organic solvent such as methylene chloride.

When R is (CH$_2$)$_4$NHCbZ (CbZ=benzyloxycarbonyl) the removal of the CbZ blocking group is carried out by treatment with boron tribromide.

When R' is tertiary alkyl the conversion of 3 to 4 may be carried out by the action of an aprotic acid, for example, by refluxing trifluoroacetic acid.

Alternatively, compounds of type 4 may be prepared by Schotten-Baumann reaction of the acid halide (2, X=halide) with the amino acid in the presence of a weak base, preferably sodium or potassium bicarbonate, in aqueous solution, as in the following reaction scheme:

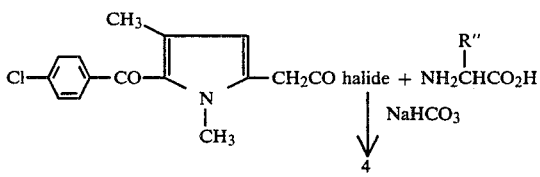

The salts of the compounds of general formula 4 may be prepared by the conventional method of reacting the acid compounds 4 with the desired base, or by cation exchange.

Analgesic activity of compounds of the instant invention can be demonstrated using the mouse acetylcholine bromide-induced writhing test [H. O. J. Collier, L. C. Deneen, C. A. Johnson and C. Schneider, Brit. J. Pharmacol. Chemother. 32, 295 (1968)]at doses of about 0.5 to 5 mg/kg, p.o.

The antiinflammatory activity of the compounds of the instant invention was measured using the rat adjuvant arthritis test [S. Wong, J. F. Gardocki and T. P. Pruss, J. Pharmacol. and Exp. Ther. 185, 127 (1973)]. Female Wistar/Lewis rats were given an injection of heat-killed Mycobacterium butyricum in light mineral oil. After 11 days, the animals which had developed an arthritic condition were selected and given daily oral doses of test drug for 4 days. Paw volumes were measured and the percent inhibition of the noninjected hind paw as compared to controls was calculated. The results (Table I) are expressed as ED$_{50}$ (mg/kg/day).

In addition to their antiinflammatory activity, the compounds were evaluated for their ability to induce gastric ulceration since gastric irritation is the most significant side effect following administration of prostaglandin biosynthesis inhibitors. As described by Wong et al., the dose (UD$_{50}$ mg/kg/day) required to produce 50 percent ulcerogenic response following 4 days of oral dosing with test drug was determined. The results are shown in Table I.

As described by Wong et al., a therapeutic index in respect to gastric ulceration, the "antiinflammatory index (AII)" defined as UD$_{50}$/ED$_{50}$, was determined. The results in Table I demonstrate unexpected safety of the compounds of the instant invention.

TABLE I

| Example No. | Compound** | ED$_{50}$ | UD$_{50}$ | AII |
|---|---|---|---|---|
| | zomepirac | 0.51 | 13.8 | 27.2 |
| VII | 4, R" = H | 0.61 | 21.1* | 34.4 |
| VIII (1) | 4, R" = CH$_3$ | 0.67 | 25.4* | 37.6 |
| XI | 4, R" = (CH$_2$)$_2$CONH$_2$ | 0.72 | 33.4* | 46.5 |
| VIII (2) | 4, R" = (CH$_2$)$_2$SCH$_3$ | 0.93 | 43.7* | 46.9 |
| VIII (3) | 4, R" = (CH$_2$)$_2$CO$_2$H | 0.54 | 37.0* | 68.9* |
| X | 4, R" = (CH$_2$)$_4$NH$_2$ | 0.64 | 35.1* | 54.8* |
| VIII (4) | 4, R"= CH$_2$CO$_2$H | 0.76 | 71.0* | 93.1* |

*Significantly different from parent compound p ≦0.05
**The compounds were all administered as aqueous solutions of their sodium salts.

The compounds of formula 4 may be administered to humans in the same general manner as zomepirac in a per unit dose range from about 10 to 100 mg.

The following examples are intended to illustrate, but not to limit, the scope of the present invention.

EXAMPLE I

Cyanomethyl [5-(4-Chlorobenzoyl)-1,4-dimethyl-1H-pyrrol-2-yl]-acetate

A 21 ml (0.33 mole) sample of chloroacetonitrile was added to a suspension of 100 g (0.28 mole) sodium [5-(4-chlorobenzoyl)-1,4-dimethyl-1H-pyrrol-2-yl]-acetate in 1.3 1 DMSO. The reaction mixture was stirred for 5 hours. The reaction mixture was poured into water. The precipitate was collected, taken up in methylene chloride, washed with sodium bicarbonate solution, and dried over anhydrous potassium carbonate. The methylene chloride was stripped off in vacuo giving a yellow solid which upon recrystallization from toluene yielded 74.6 g of cyanomethyl [5-(4-chlorobenzoyl)-1,4-dimethyl-1H-pyrrol-2-yl] acetate (80% yield), m.p. 133°–136° C.

EXAMPLE II

Methyl N-{[5(4-chlorobenzoyl)-1,4-dimethyl-1H-pyrrol-2-yl]acetyl}alaninate

A solution of 10.0 g (0.03 mole) of cyanomethyl [5-(4-chlorobenzoyl)-1,4-dimethyl-1H-pyrrol-2-yl]acetate, 1.6 g (0.015 mole) of alanine methyl ester hydrochloride, 0.3 ml of glacial acetic acid, and 2.1 ml (0.015 mole) triethylamine in 40 ml of THF was heated under reflux for 3½ hours. A second addition of 1.6 g of alanine methyl ester hydrochloride and 2.1 ml of triethylamine was made. The mixture was heated under reflux for 2 hours. A fourth addition of 2.0 g (0.018 mole) of triethylamine was made. The mixture was heated under reflux for 16 hours. The reaction was partitioned between chloroform and dilute hydrochloric acid. The organic layer was washed with brine and dried over anhydrous magnesium sulfate. The solvent was evaporated in vacuo. The residue was recrystallized from acetonitrile to give 9.6 g of methyl N-{[5-(4-chlorobenzoyl)-1,4-dimethyl-1H-pyrrol-2-yl]acetyl}alaninate, m.p. 163°-165° C. (85% yield).

EXAMPLE III

Using the procedure of Example II, employing the following amino acid ester salts in place of alanine methyl ester hydrochloride and allowing them to react with cyanomethyl [5-(4-chlorobenzoyl)-1,4-dimethyl-1H-pyrrol-2-yl]acetate in the presence of triethylamine, the respective [5-(4-chlorobenzoyl-1,4-dimethyl-1H-pyrrol-2-yl]acetyl derivatives of the amino acid esters were prepared:

| Starting Material (Molar equivalents) | Product | Reaction time (hours) | % Yield | m.p. °C. |
|---|---|---|---|---|
| Methionine methyl ester hydrochloride (2) | Methyl N—{[(5-(4-chlorobenzoyl)-1,4-dimethyl-1H—pyrrol-2-yl]-acetyl}-methioninate | 49 | 78 | 125-6 |
| Aspartic acid dimethyl ester hydrochloride (1.5) | Dimethyl N—{[5-(4-chlorobenzoyl)-1,4-dimethyl-1H—pyrrol-2-yl]-acetyl} aspartate | 7 | 60 | 160-161 |
| $N^6$—(benzyloxycarbonyl) lysine benzyl ester hydrochloride | Benzyl $N^6$—benzyloxycarbonyl-$N^2${[5-(4-chlorobenzoyl)-1,4-dimethyl-1H—pyrrol-2-yl]-acetyl}lysinate | 22 | 50 | 103-104 |

EXAMPLE IV

Using the procedure of Example II, employing the following amino acid esters in place of alanine methyl ester, and causing them to react with cyanomethyl [5-(4-chlorobenzoyl)-1,4-dimethyl-1H-pyrrol-2-yl]-acetate in the presence of triethylamine, the corresponding [5-(4-chlorobenzoyl)-1,4-dimethyl-1H-pyrrol-2-yl]-acetyl amino acid esters may be prepared respectively:

| Amino Acid Ester | Product |
|---|---|
| L-valine methyl ester hydrochloride | Methyl N—{[5-(4-chlorobenzoyl)-1,4-dimethyl-1H—pyrrol-2-yl]-acetyl}-valinate |
| L-leucine methyl ester hydrochloride | Methyl N—{[5-(4-chlorobenzoyl)-1,4-dimethyl-1H—pyrrol-2-yl]-acetyl}-leucinate |
| L-isoleucine methyl ester hydrochloride | Methyl N—{[5-(4-chlorobenzoyl)-1,4-dimethyl-1H—pyrrol-2-yl]-acetyl}-isoleucinate |

EXAMPLE V

Dimethyl N-{[5-(4-chlorobenzoyl)-1,4-dimethyl-1H-pyrrol-2-yl]}-acetyl-glutamate

To a suspension of 30.45 g (0.098 mole) [5-(4-chlorobenzoyl)-1,4-dimethyl-1H-pyrrol-2-yl]-acetic acid in 120 ml dry THF was added 1.4 ml (0.098 mole) of N-methylmorpholine. The mixture was cooled to −65° C. A 10 ml (0.098 mole) sample of ethyl chloroformate in 50 ml of dry THF was added dropwise to the reaction mixture maintaining the temperature at −65° C. The mixture was stirred for ½ hour after the addition was completed. Then, 32.32 g (0.15 mole) of L-glutamic acid dimethyl ester hydrochloride was partitioned between 150 ml of 20% potassium carbonate and 275 ml tetrahydrofuran. The tetrahydrofuran layer was separated and dried over 4A molecular sieves and anhydrous sodium sulfate.

The resulting L-glutamic acid dimethyl ester solution was added to the reaction mixture as quickly as possible maintaining the temperature at −65° C. It was allowed to stir for 3½ hours at −65° C. then warmed to room temperature and stirred overnight. The reaction mixture was poured into 3N hydrochloric acid, extracted into chloroform, washed with sodium bicarbonate solution, water, brine and dried over anhydrous sodium sulfate. The chloroform was evaporated in vacuo giving a yellow solid, dimethyl N-{[5-(4-chlorobenzoyl)-1,4-dimethyl-1H-pyrrol-2-yl]acetyl}-glutamate (45.7%) m.p. 129°-130.5° C.

EXAMPLE VI

Methyl N{[5-(4-chlorobenzoyl)-1,4-dimethyl-1H-pyrrol-2-yl]-acetyl}-glycinate

A 22.6 ml (0.16 mole) sample of triethylamine was added to a suspension of 6.78 g (0.054 mole) of glycine methyl ester hydrochloride in 200 ml of spectral grade chloroform. The mixture was cooled to 0° C. and a solution of 16.8 g (0.54 mole) of [5-(4-chlorobenzoyl)-1,4-dimethyl-1H-pyrrol-2-yl]-acetyl chloride in 80 ml of chloroform was added slowly. The mixture was stirred at room temperature overnight. The solution was washed successively with dilute hydrochloric acid and water and dried over anhydrous magnesium sulfate. The solvent was evaporated in vacuo. The residue was recrystallized successively from methanol and acetonitrile to give 9.2 g (47% yield) of crystalline methyl N-{[5-(4-chlorobenzoyl)-1,4-dimethyl-1H-pyrrol-2-yl]-acetyl}-glycinate, m.p. 198°-201° C.

EXAMPLE VII

N-{[5-(4-chlorobenzoyl)-1,4-dimethyl-1H-pyrrol-2-yl]-acetyl}-glycine

To a solution of 8.55 g (0.0236 mole) of methyl N-{[5-(4-chlorobenzoyl)-1,4-dimethyl-1H-pyrrol-2-yl]-acetyl}-glycinate in 50 ml of refluxing methanol was added 49.2 ml of 0.5 normal sodium hydroxide. The solution was heated under reflux for 30 minutes. The mixture was poured into dilute hydrochloric acid. The precipitate was collected and dried. It was recrystallized successively from ethanol and methanol to give 6.2 g (75% yield) of white crystalline N-[5-(4-chlorobenzoyl)-1,4-dimethyl-1H-pyrrol-2-yl]-acetyl}-glycine, m.p. 206°-208° C.

Anal. Calc'd for $C_{17}H_{17}ClN_2O_4$: C, 58.54; H, 4.91. Found: C, 58.42; H, 5.03.

EXAMPLE VIII

Using the procedure of Example VII, employing the N-[5-(4-chlorobenzoyl)-1,4-dimethyl-1H-pyrrol-2-yl]-acetyl derivatives of the amino acid methyl esters from Examples II, III and V in place of methyl N-{[5-(4-chlorobenzoyl)-1,4-dimethyl-1H-pyrrol-2-yl]-acetyl}-glycinate and employing one equivalent of sodium hydroxide for each saponifiable ester group, the following N-[5-(4-chlorobenzoyl)-1,4-dimethyl-1H-pyrrol-2-yl]- acetyl derivatives of amino acids were prepared respectively.

| | % Yield | m.p. °C. |
|---|---|---|
| N—{[5-(4-chlorobenzoyl)-1,4-dimethyl-1H—pyrrol-2-yl]-acetyl}-alanine | 56 | 222–223° |
| N—{[5-(4-chlorobenzoyl)-1,4-dimethyl-1H—pyrrol-2-yl]-acetyl}-methionine | 60 | 184–185° |
| N—{[5-(4-chlorobenzoyl)-1,4-dimethyl-1H—pyrrol-2-yl]-acetyl}-glutamic acid | 11 | 194–196° |
| N—{[5-(4-chlorobenzoyl)-1,4-dimethyl-1H—pyrrol-2-yl]-acetyl}-aspartic acid | 42 | 219–220° |

EXAMPLE IX

Using the procedure of Example VII and employing the N-[5-(4-chlorobenzoyl)-1,4-dimethyl-1H-pyrrol-2-yl]-acetyl amino acid methyl esters from Example IV, the following products may be obtained respectively:

N-{[5-(4-chlorobenzoyl)-1,4-dimethyl-1H-pyrrol-2-yl]-acetyl}-valine

N-{[5-(4-chlorobenzoyl)-1,4-dimethyl-1H-pyrrol-2-yl]-acetyl}-leucine

N-{[5-(4-chlorobenzoyl)-1,4-dimethyl-1H-pyrrol-2-yl]-acetyl}-isoleucine

EXAMPLE X $N^2$-{[5-(4-chlorobenzoyl)-1,4-dimethyl-1H-pyrrol-2-yl]-acetyl}-lysine-hydrate (5:8)

A solution of 3.7 g (5.7 mmoles) of benzyl $N^6$-benzyloxycarbonyl-$N^2$-{[5-(4-chlorobenzoyl)-1,4-dimethyl-1H-pyrrol-2-yl]-acetyl}-lysinate in 75 ml of methylene chloride was cooled at −70°. A solution of 35.7 ml of 1M boron tribromide in methylene chloride was added in portions and the mixture stirred at −70° for 3 hours. The reaction was allowed to warm to room temperature over one hour. Water was added. The aqueous layer was adjusted to pH 7.5 by the addition of 1N NaOH solution. The precipitated solid was collected and recrystallized from ethanol-water (2:1) to give 1.5 g (50% yield) of $N^2$-{[5-(4-chlorobenzoyl)-1,4-dimethyl-1H-pyrrol-2-yl]-acetyl}-lysine hydrate (5:8) m.p. 252°–253° C.

Anal. Calc'd for $C_{21}H_{26}ClN_3O_4$: C, 56.19; H, 6.20; N, 9.36. Found: C, 55.97; H, 6.59; N, 9.07.

EXAMPLE XI

N-{[5-(4-chlorobenzoyl)-1,4-dimethyl-1H-pyrrol-2-yl]-acetyl}-glutamine

A solution of 30.5 g (0.1 mole) of [5-(4-chlorobenzoyl)-1,4-dimethyl-1H-pyrrol-2-yl]-acetyl chloride in 150 ml of dioxane was added slowly at 0°–5° C. to a suspension of 5.88 g (0.15 mole) of magnesium oxide and 14.3 g (0.1 mole) of L-glutamine in 300 ml of water. The resulting yellow suspension was stirred at room temperature for 64 hours. The mixture was acidified with 1N hydrochloric acid and cooled. The precipitate was collected, washed with water and air dried. It was recrystallized three times from 2-propanol to give 10.8 g of light tan solid which was subjected to chromatography on silica gel. The column was eluted with chloroform:acetic acid:methanol (95:05:4.5). The major compound bearing fraction was concentrated to dryness and the residue recrystallized from acetone, water (2:1) to give 4.5 g (10% yield) of pale yellow crystalline N-{[5-(4-chlorobenzoyl)-1,4-dimethyl-1H-pyrrol-2-yl]-acetyl}-glutamine, hydrate (1:1), m.p. 186°–188° C.

Anal. Calc'd for $C_{20}H_{22}ClN_2O_5 \cdot H_2O$: C. 54.86; H, 5.52: $H_2O$, 4.11. Found: C, 54.75; H, 5.42; $H_2O$, 4.30.

EXAMPLE XII

Salts of N-{[5-(4-Chlorobenzoyl)-1,4-dimethyl-1H-pyrrol-2-yl]-acetyl}-aminoacids (A) By treating the acylamino acid from Example VII with 5N NaOH and filtering the solid, the following sodium salt may be obtained: Sodium N-{[5-(4-chlorobenzoyl)-1,4-dimethyl-1H-pyrrol-2-yl]-acetyl}-glycinate. The alkali metal salts of the acids from Examples VIII–XI may be obtained in a similar manner.

(B) By treating the acylamino acids from Example VII with 2-amino-2-(hydroxymethyl)-1,3-propanediol in alcoholic solution and concentrating the solution, the following tromethamine salt may be prepared: 2-ammonium-2-hydroxymethyl-1,3-propanediol N-{[5-(4-chlorobenzoyl)-1,4-dimethyl-1H-pyrrol-2-yl]-acetyl}-alaninate. The tromethamine salts of the acids from Examples VIII–XI may be obtained in a similar manner.

(C) By dissolving the acylamino acids from Example VII in one equivalent of aqueous tromethamine and adding aqueous calcium chloride solution, the following calcium salt may be obtained: calcium N-{[5-(4-chlorobenzoyl)-1,4-dimethyl-1H-pyrrol-2-yl]-acetyl}-methioninate [1:2]. The calcium salts of the acids from Examples VIII-XI may be obtained in a similar manner.

What is claimed is:

1. A pyrrole-2-acetylamino acid compound of the following formula:

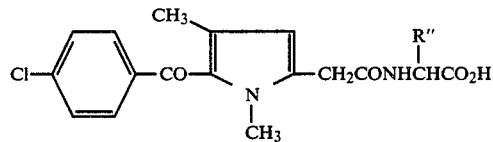

or pharmaceutically acceptable salt thereof, wherein R″ is $(CH_2)_4NH_2$.

2. A compound according to claim 1, which is $N^2$-{[5-(4-chlorobenzoyl)-1,4-dimethyl-1H-pyrrol-2-acetyl}-lysine.

3. An amide ester compound of the following formula:

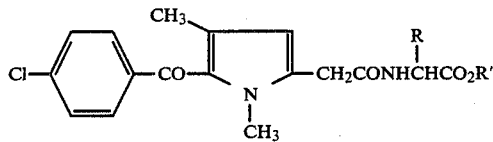

wherein
R is $(CH_2)_4$NHCOO benzyl, and
R′ is alkyl or benzyl.

4. An amide according to claim 3, which is benzyl $N^6$-benzyloxycarbonyl-$N^2$-{5-4-chlorobenzoyl)-1,4-dimethyl-1H-pyrrol-2-yl-acetyl}-lysinate.

5. A pharmaceutical composition which comprises a compound according to claim 1 in association with a pharmaceutically acceptable diluent or carrier.

6. A method for treating inflamation in an animal which comprises administering to the animal a pharmaceutically effective amount of the pharmaceutical composition of claim 5.

7. A method of treating pain in an animal which comprises administering to the animal a pharmaceutically effective amount of the pharmaceutical composition of claim 5.

* * * * *